(12) United States Patent
Culp

(10) Patent No.: US 10,195,690 B2
(45) Date of Patent: *Feb. 5, 2019

(54) LASER CUTTING

(71) Applicant: Align Technology, Inc., San Jose, CA (US)

(72) Inventor: James C. Culp, Pleasanton, CA (US)

(73) Assignee: Align Technology, Inc., San Jose, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 15/218,778

(22) Filed: Jul. 25, 2016

(65) Prior Publication Data

US 2016/0332255 A1 Nov. 17, 2016

Related U.S. Application Data

(63) Continuation of application No. 13/239,173, filed on Sep. 21, 2011, now Pat. No. 9,403,238.

(51) Int. Cl.
*B23K 26/06* (2014.01)
*B23K 26/08* (2014.01)
(Continued)

(52) U.S. Cl.
CPC ........ *B23K 26/0626* (2013.01); *B23K 26/064* (2015.10); *B23K 26/08* (2013.01); *B23K 26/083* (2013.01); *B23K 26/0853* (2013.01); *B23K 26/0861* (2013.01); *B23K 26/142* (2015.10); *B23K 26/38* (2013.01)

(58) Field of Classification Search
None
See application file for complete search history.

(56) References Cited

U.S. PATENT DOCUMENTS

| 4,638,145 A | 1/1987 | Sakuma et al. |
| 5,061,839 A | 10/1991 | Matsuno et al. |

(Continued)

FOREIGN PATENT DOCUMENTS

| CN | 101095099 A | 12/2007 |
| CN | 101188981 A | 5/2008 |

(Continued)

OTHER PUBLICATIONS

Office Action from related Chinese Patent Application 201280045915, dated Jun. 2, 2016, 17 pp.

(Continued)

*Primary Examiner* — Jason Lin
(74) *Attorney, Agent, or Firm* — Brooks, Cameron & Huebsch, PLLC

(57) ABSTRACT

Laser cutting systems and methods are described herein. One or more systems include a laser generating component, an optical component, a fixture for holding a support with a part positioned on the support, and a control mechanism for adjusting at least one of the laser generating component, the optical component, and the fixture such that a ratio of a laser energy applied to the part and a part material thickness is maintained within a predetermined acceptable range at each point along a cut path to cut through the part while maintaining the integrity of the support. Other systems and methods are disclosed herein.

6 Claims, 7 Drawing Sheets

(51) Int. Cl.
*B23K 26/38* (2014.01)
*B23K 26/142* (2014.01)
*B23K 26/064* (2014.01)

(56) References Cited

U.S. PATENT DOCUMENTS

| | | | |
|---|---|---|---|
| 5,224,049 A * | 6/1993 | Mushabac | A61C 13/0004 |
| | | | 264/222 |
| 6,002,706 A | 12/1999 | Staver et al. | |
| 6,313,432 B1 * | 11/2001 | Nagata | B23K 26/12 |
| | | | 219/121.67 |
| 6,414,264 B1 * | 7/2002 | von Falkenhausen | |
| | | | A61K 9/7023 |
| | | | 219/121.72 |
| 6,462,301 B1 * | 10/2002 | Scott | B23K 26/04 |
| | | | 219/121.6 |
| 7,257,136 B2 | 8/2007 | Mori et al. | |
| 7,435,083 B2 | 10/2008 | Chishti et al. | |
| 7,711,447 B2 | 5/2010 | Lu et al. | |
| 8,601,925 B1 * | 12/2013 | Coto | B23D 45/042 |
| | | | 83/360 |
| 2003/0000927 A1 * | 1/2003 | Kanaya | B23K 26/04 |
| | | | 219/121.7 |
| 2003/0019848 A1 | 1/2003 | Nicholas et al. | |
| 2003/0057192 A1 | 3/2003 | Patel | |
| 2003/0192867 A1 * | 10/2003 | Yamazaki | B23K 26/08 |
| | | | 219/121.78 |
| 2004/0197728 A1 | 10/2004 | Abolfathi et al. | |
| 2005/0171630 A1 | 8/2005 | Dinauer et al. | |
| 2006/0137813 A1 * | 6/2006 | Robrecht | B32B 37/206 |
| | | | 156/256 |
| 2006/0199153 A1 | 9/2006 | Liu et al. | |
| 2007/0199929 A1 * | 8/2007 | Rippl | B23K 26/04 |
| | | | 219/121.78 |
| 2007/0215582 A1 * | 9/2007 | Roeper | B01L 3/5023 |
| | | | 219/121.69 |
| 2009/0103579 A1 | 4/2009 | Ushimaru et al. | |
| 2010/0193482 A1 * | 8/2010 | Ow | B23K 26/38 |
| | | | 219/121.67 |
| 2010/0327461 A1 | 12/2010 | Fukumitsu | |
| 2011/0056350 A1 * | 3/2011 | Gale | B23K 26/0823 |
| | | | 83/54 |
| 2011/0220623 A1 * | 9/2011 | Beutler | B23K 26/0876 |
| | | | 219/121.67 |

FOREIGN PATENT DOCUMENTS

| | | |
|---|---|---|
| DE | 4207169 | 9/1993 |
| EP | 1362667 | 11/2003 |
| JP | 2008531234 | 8/2008 |
| JP | 2009101386 | 5/2009 |
| JP | 2010017726 A | 1/2010 |
| KR | 200262793 | 3/2002 |
| KR | 200262793 | 5/2009 |
| KR | 20090065778 | 6/2009 |
| KR | 20090065778 | 6/2010 |
| WO | 2006071499 A2 | 7/2006 |
| WO | 2006096558 | 9/2006 |
| WO | 2007071341 | 6/2007 |
| WO | 2009016645 | 2/2009 |

OTHER PUBLICATIONS

International Search Report corresponding to International Patent Application PCT/IB2012/001812, dated Jan. 30, 2013.
Office Action from related China Patent Application No. 201280045915, dated Dec. 8, 2016, 21 pp.
Notice of Preliminary Rejection from related Korean Application No. 10-2014-7010353, dated Mar. 21, 2018, 20 pages.
Office Action from related Canadian Application No. 2855738, dated Dec. 12, 2018, 10 pages.

* cited by examiner

LASER CUTTING

PRIORITY INFORMATION

The present application is a continuation of U.S. patent application Ser. No. 13/239,173, filed on Sep. 21, 2011, the contents of which are incorporated herein by reference.

TECHNICAL FIELD

The present disclosure relates to systems and methods for laser cutting.

BACKGROUND

Laser cutting systems have been devised and are utilized in many industries. For example, in the auto industry a laser cutting system is used to cut the edging on a bumper that is formed using a mold, stamping press, or other forming tool.

Once formed, the bumper is removed from the mold, press, etc., but often includes some extra material around the edges from the mold formation process. A laser cutting system can be used to remove this extra material from the bumper. Accordingly, the laser cuts the material off and the edge of the part is polished through hand polishing, or other such manners, to remove any sharp portions and generally smooth the edge.

In some other implementations, an item is formed on a mold and a laser is used to cut the item off of the mold. Alternatively, an item is formed on a mold by stamping or another forming process and the item is positioned using a support of some kind. If the item has been molded, the mold may be used as the support. However, cutting into the support material can be detrimental to the process. For instance, the support material, when cut with the laser, may mix with the material used to form the item. This can cause unintended material physical characteristics or discoloration, which may not be desirable.

The cutting process itself can also change the characteristics of the material near the cut path. Unlike other cutting techniques, laser cutting generates enough heat to cut the material and, as such, the material's interaction with the heat can change its characteristics, for example, making it more brittle which can be undesirable in some applications. This can be particularly true where the cut is to be made at relatively high speed and therefore a high energy laser beam is used to cut through the material quickly.

Additionally, the thickness of the material being cut can change in some implementations and as such, the effectiveness of the cutting technique can be reduced. For example, if a portion of the material being cut is thicker than a portion used to calibrate the laser for most effective cutting, the laser may not cut all the way through the material or the material may not be vaporized as effectively.

If the material is thinner, the characteristics of the edge of the cut material may be changed in an unintended manner. The laser may also cut through the item being cut and into the support material which may be undesirable in some applications as discussed above.

DETAILED DESCRIPTION

Laser cutting systems and methods are described herein. For example, one or more systems include a laser generating component, an optical component, a fixture for holding a support with a part positioned on the support, and a control mechanism for adjusting at least one of the laser generating component, the optical component, and the fixture such that a ratio of a laser energy applied to the part and a part material thickness is maintained within a predetermined acceptable range at each point along a cut path to cut through the part while maintaining the integrity of the support. Other systems and methods are disclosed herein.

Embodiments of the present disclosure can cut through a material for forming a part without cutting into a support material adjacent to the part material. In some embodiments, the laser beam can cut through the part material, but not substantially into the support material. In such instances, it may provide a part that is cut and is not substantially mixed with material from the support and/or may allow for reuse of the support, if desired.

Embodiments are provided herein that allow for a part to be cut quickly without a substantial change to the characteristics of the edge of the part near the cut path made by the laser beam, such as the brittleness or discoloration of the part. Embodiments can also cut through materials having different thicknesses that are adjacent to a support, among other benefits. This can be accomplished by changing one or more characteristics of the laser beam as described in more detail below.

In the following detailed description, reference is made to the accompanying drawings that form a part hereof. The drawings show, by way of illustration, how one or more embodiments of the disclosure may be practiced.

Figure 1:
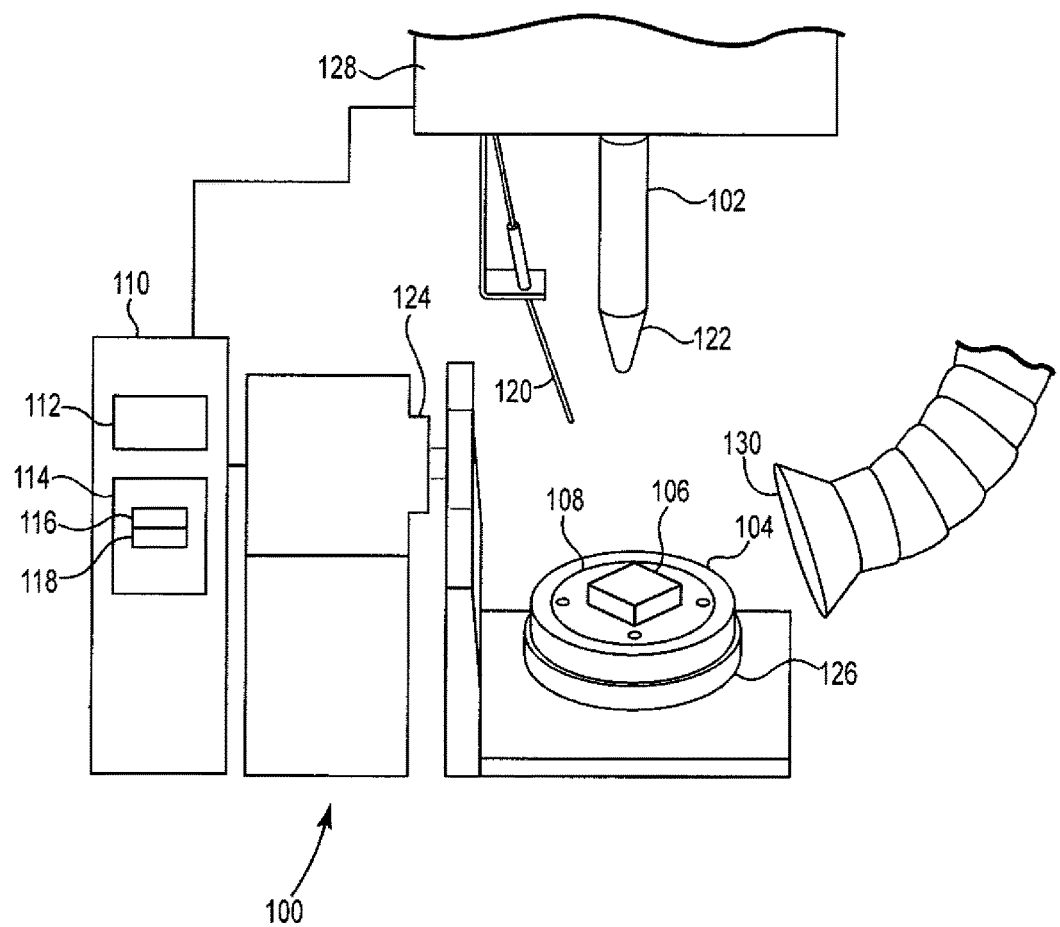
FIG. 1 illustrates a system that can be used in accordance with one or more embodiments of the present disclosure.

FIG. 1 illustrates a system that can be used in accordance with one or more embodiments of the present disclosure. In the embodiment illustrated in FIG. 1, the system 100 is provided for laser cutting a part from a piece of part material formed over a mold 106.

The system 100 of FIG. 1 includes a laser generating component 102, one or more optical components 122, a fixture 104, and a mold 106 positioned on the fixture 104. In the embodiment of FIG. 1, the fixture also includes a platform 108 for positioning the mold 106 thereon and a rotating mechanism 126 that allows the part to rotate in a clockwise and/or counterclockwise direction when viewed from above the platform.

In the embodiment of FIG. 1, the system 100 also includes a control component 110. The control component 110 includes a processor 112, memory 114, and one or more control mechanisms 124, 126, and/or 128. Instructions 116 can be stored in the memory 114 and executed by the processor 112 to control, for example, movement of the fixture 104 holding the part, movement of the laser generating component 102, movement of one or more of the optical components 122, adjustment of one or more characteristics of the laser beam generated by the laser generating component 102, adjustment of the characteristics of a gas applied via nozzle 120 and/or other characteristics of a suction applied via tube 130.

These items can be controlled, for example, via control components 124, 126, and/or 128 and/or via mechanisms provided to adjust one or more optical components 122, adjust characteristics of the laser generating component 102, adjust characteristics of a gas provided via nozzle 120, and/or adjust suction pressure provided via suction tube 130. Memory 114 can also have data 118 stored therein that can be used in executing the instructions as will be discussed in more detail below.

Memory can be a non-transitory machine readable medium that provides volatile or nonvolatile memory. The memory can also be removable, e.g., portable memory, or non-removable, e.g., internal memory. For example, the memory can be random access memory (RAM) or read-only memory (ROM).

Memory can, for example, be dynamic random access memory (DRAM), electrically erasable programmable read-only memory (EEPROM), flash memory, phase change random access memory (PCRAM), compact-disk read-only memory (CD-ROM), a laser disk, a digital versatile disk (DVD) or other optical disk storage, and/or a magnetic medium such as magnetic cassettes, tapes, or disks, among other types of memory.

Further, although memory is illustrated as being located in a control mechanism 110, embodiments of the present disclosure are not so limited. For example, memory can also be located in a memory device that is not a control mechanism, but is connected to the control mechanism. In some embodiments, the memory can be internal or external to a computing resource and can enable machine readable instructions to be uploaded and/or downloaded over a network, such as the Internet, or another wired or wireless connection.

With respect to the control of the laser generating component, the energy of the laser beam can be controlled in various manners. For example, the power to the laser generating component can be adjusted to increase the energy of the beam created.

For instance, the energy to be applied to the part can be controlled within a predetermined range by modulating the power of the laser beam, adjusting an optical component (e.g., one or more mirrors and/or lenses), and/or controlling the speed of the fixture and/or laser generating component relative to the fixture based on the part characteristics and the desired cutting path. The combination of these elements can be varied depending upon the characteristics of the system and/or the characteristics of the materials being cut. For example, if the system does not have a laser generating component that is adjustable with regard to its energy, then the speed of the movement of the fixture and/or the laser generating component and/or one or more optical components can be adjusted.

As discussed above, an adjustment that can be made is with respect to the optical components used. By changing components (e.g., switching lenses), or adjusting them (e.g., changing the focal length and/or moving the optical components), the energy generated by the laser generating component can be changed as it passes through or is directed by one or more optical components.

These movements can be controlled by the one or more control mechanisms illustrated in FIG. 1 and/or by the executable instructions stored in memory. For example, a five inch focal length may be used, but it may be adjusted to a shorter or longer length. This focal length can be beneficial for applications such as cutting dental appliances as it allows for a good amount of variability and can maintain a high enough laser energy at focus to adequately vaporize the part material.

The control component 110 can include a fixture control (e.g., software and electrical and/or mechanical actuators) that adjusts a speed of the fixture and wherein the control component receives data regarding the part material thickness, at multiple points along a cut path where the laser beam will cut the part, and adjusts a speed of movement of the part past the laser beam based on the thickness data such that the ratio of the laser energy applied to the part and the part material thickness is maintained within the predetermined acceptable range.

In such embodiments, the ratio can be predetermined or determined dynamically based upon thickness data and/or laser power data taken during the cutting process. The acceptable range of the ratio is based on the laser energy needed to cut through the part material without cutting into the support material, or in some instances, without cutting into the support material to such an extent as to either damage the support or facilitate the mixing of support material with the part material.

As used herein, a support material can include material on which items are molded, within which items are molded, under which items are molded, or upon which items are positioned after molding, such as a backing material used to hold a part for cutting. The ratio can be determined, for example, based on at least one of one or more part material characteristics and one or more characteristics of a backing material. In some such embodiments, the part, support, and/or backing material characteristics may include at least one of a composition of the material and/or the thickness of the material, for example.

In some embodiments, the part material may include multiple parts (e.g., layer material). For example, the multiple parts may be bonded together or adhered together. For instance, the part may include an intermediate layer (e.g., light adhesive or silicon) between the support (e.g., mold) and the aligner material to allow for the material (e.g., thermal formed material) to shape and cure or be removed after curing. In some embodiments, the intermediate layer can act as a buffer thickness and/or provide a different reaction to the laser to ensure that only the part material is cut and not the support.

One example of how a ratio may be applied in practice is provided below. With respect to a laser having a 9.3 micron wavelength, set at a repetition rate in the range of 15,000 and 25,000 and having an output beam size in the range of 1-4 mm, the laser has a desired output range of between 8 and 15 watts because this range of unfocused output power allows for cutting the part material without discoloring the material by applying too much laser energy to the support material beneath the part. For example, when using a rapid prototyping material (e.g., SLA material) as a mold material, the interaction of the mold material and the laser beam can cause the mold material to mix with the part material. In some instances, this may result in discoloration.

The control component 110 can include a laser power adjustment control that receives data regarding the part material thickness, at multiple points along the cut path where the laser beam will cut the part, and adjusts a power of the laser generating component based on the thickness data such that the ratio of the laser energy applied to the part and the part material thickness is maintained within the predetermined acceptable range as discussed above.

The control component 110 can include an optics control that adjusts a position of one or more of the number of optical components where the control component receives data regarding the part material thickness, at multiple points along a cut path where the laser beam will cut the part, and adjusts a position of the one or more of the number of optical components based on the thickness data such that the ratio of the laser energy applied to the part and the part material thickness is maintained within the predetermined acceptable range as discussed above.

A single control component can be utilized to control all of the above functionalities, or these functionalities can be controlled by multiple components (e.g., processors). In some embodiments, the speed of the part at the cutting position relative to the laser beam at the cutting position can be maintained substantially constant while the part is movable in at least three axes of movement and the power of the laser beam is controlled within a given range based on information about one or more characteristics of at least one of the part material, a support, and backing material.

These characteristics can be provided to the processor of the control component via memory, and/or can be provided by a user via a user interface in communication with the control component. In various embodiments, the control component can adjust the speed of the fixture such that the laser energy vaporizes all material of the part at each point along the cut path on the part while maintaining the integrity of the support.

In some embodiments, the control component for adjusting the laser energy provides a mechanism for adjusting at least one of laser generating component power, laser generating component movement, optical component type, optical component movement, fixture movement, gas type, gas pressure, gas temperature, and suction such that a ratio of a laser energy applied to the part and a part material thickness is maintained within a predetermined acceptable range.

In some such embodiments, the laser energy applied to the part thickness is maintained as the part moves at a constant or substantially constant feed rate. This can be beneficial in that the laser energy making the cut is generally distributed in an even manner as the laser beam progresses along the cut path, among other benefits. An example of a substantially constant feed rate can, for example, be 1000-1500 mm/sec. Another example includes using a 10.6 micron wavelength laser that can run at 5-10 W and have a constant feed rate of between 1500 and 2000 mm/sec. Such a configuration may allow for reduced brittleness at the edge of the cut path, in some applications.

In some embodiments, the laser energy applied to the part thickness is maintained by increasing the laser generating component power. This can be beneficial in instances where the speed of the movement of the fixture and/or laser beam cannot be adjusted, among other benefits.

The laser energy applied to the part thickness can be maintained by adjusting the optical component to create a stronger or weaker laser energy applied to the part, in some embodiments. This can be beneficial, for example, because movement of the optical components can be a more cost effective approach to adjusting the laser energy than other arrangements, such as movement of the laser and/or fixture, among other benefits.

Further, in some embodiments, if the overall power of the laser is low compared to its output potential, a beam splitter can be utilized to raise the output percentage of the power generated by the laser generating component. This can allow the laser generating component to operate in a more stable range in relationship to its duty cycle, in some instances. This may increase the durability of the system by operating the laser in its mid power range (e.g., 40-60%, while delivery to the cut location may be as low as 10% due to the splitting of the beam), in some applications. Another benefit of this arrangement can be the reduction of laser pulsing (i.e., a fluctuation in laser energy) because the laser in not operating at a low power, in some instances.

Additionally, the use of a lower energy with respect to the cut location can reduce the presence of several phenomena that cause brittleness. For example, reforming the heated part material (i.e., a region next to the edge of the cut that is smooth and shiny due to melting and cooling), mounding or lipping (i.e., a region next to the edge of the cut that forms a raised smooth and shiny beaded edge), and recasting (i.e., an edge that is rough and has remnants of the molten material as it is blown off its resting point by gas from the gas nozzle, if used).

The control mechanisms that are used to adjust the various components of the system can be any suitable mechanisms. For example, they can be electrical and/or mechanical actuators that move one component with respect to another component of the system 100. For example, in the embodiment of FIG. 1, control mechanism 128 can be used to move the laser generating component 102, optical component 122, and gas nozzle 120 closer or farther with respect to the platform 108 and thereby closer to or farther from the mold 106.

Such movements can change the characteristics of the laser beam generated, how the optics interact with the beam generated, and the gas applied. In some embodiments, the nozzle 120, optical component 122, and laser generating component can each be moved independently with respect to each other.

Control mechanism 124 can, for example be a mechanical actuator that moves the fixture in a number of directions. For example, in the embodiment of FIG. 1, the mechanism 124 can move the part horizontally with respect to the laser generating component 102 and can also rotate the fixture 104 clockwise and/or counterclockwise when viewed from the side of the platform 104 (e.g., from the perspective of the suction tube 130 of FIG. 1). In the embodiment of FIG. 1, the combination of the movements of mechanism 124 and those of mechanism 126 allow the fixture to be moved in five axes of motion with respect to the laser generating component 102 as will be discussed in more detail below.

In one or more embodiments, the fixture for handling the part can, for example, include a robot suction and/or pincher mechanism to secure and/or move the support and/or part during the laser cutting process.

As illustrated in FIG. 1, in some embodiments, the system can include one or more gas nozzles (e.g., nozzle 120) which dispense gas or suck gas in. In various embodiments, the one or more nozzles can be directed at a point at which the laser energy contacts the part. The gas can be any suitable type of gas including chilled, heated, and/or room temperature gas (e.g., one type for one nozzle and another type from another nozzle). Examples can include air, oxygen, and/or nitrogen, among others.

This can be beneficial for a number of reasons. For example, gas can be used to heat or cool the part, dissipate heat generated from the laser, change the chemical composition of the gas (e.g., air) at the area of the cut, and/or suck or blow away debris from the cut path if it is not vaporized from the cutting process, among other benefits.

In various embodiments, the area affected by the heat can be reduced depending upon the direction in which the gas and laser beam are oriented. For example, area of heat effect may be reduced when the laser beam is traveling in line with the directed gas and may increase when traveling across the path of the gas exiting from the tip of the nozzle.

In some embodiments, a nozzle is located at a location remote from the laser generating component and at an angle to a direction of a laser beam that directs the laser energy toward the part. Such an embodiment is illustrated in FIG. 1, where the nozzle 120 is oriented at an angle to the laser beam generated by the laser generating component 102. This can be beneficial, in some embodiments, for example, because the gas can be used to blow away the debris from the cut path area.

Other benefits include: the surface of the cut being improved as well as clouding from the cutting process being reduced through use of blowing a gas at moderate velocity. This can, for example, move heavy particles created by cutting process away from the cut edge, among other benefits.

Nozzles can have various shapes and sizes based upon the application in which it is used. For example, the inner diameter of a nozzle, nozzle tip angle, overall angle of a nozzle to the cut location, and nozzle tip shape can be adjusted.

Nozzles can also be oriented in different positions with respect to the cutting location. For instance, a nozzle may be oriented at an angle of 32 degrees using a tube with a 1.7 mm inner diameter for debris removal. The tube can be made of brass with the tip compressed into a fan shape of approximately 1 mm height from the opening, in some embodiments. These characteristics are provided as examples and should not be limiting on the claims herein as other materials, shapes, and orientations can be used in various embodiments.

In some embodiments, the system includes a suction mechanism located proximate to where the laser energy contacts the part to remove debris created when the laser energy contacts the part. For example, one such embodiment is illustrated at FIG. 1. This can be beneficial, in some embodiments, for example, because the suction mechanism (e.g., suction tube 130) can be used to suction away the debris from the cut path area, among other benefits. This can be used in combination with one or more nozzles which, in some instances, can better remove debris from the area, for example, by blowing the debris toward the suction mechanism.

Another system embodiment includes a laser generating component for producing a laser beam, a fixture for holding a support with a part to be cut by the laser beam wherein the part is positioned on the support, an optical component for focusing the laser beam to create a predetermined range of energy at a cut path to cut through the part while not substantially cutting the support (maintaining the integrity of the support), and a controller for adjusting a laser energy applied to the part thickness wherein the controller receives data regarding the part material thickness, at multiple points along the cut path, and adjusts a ratio of the laser energy applied to the part and a part material thickness to maintain the ratio within a predetermined acceptable range.

Figure 2:
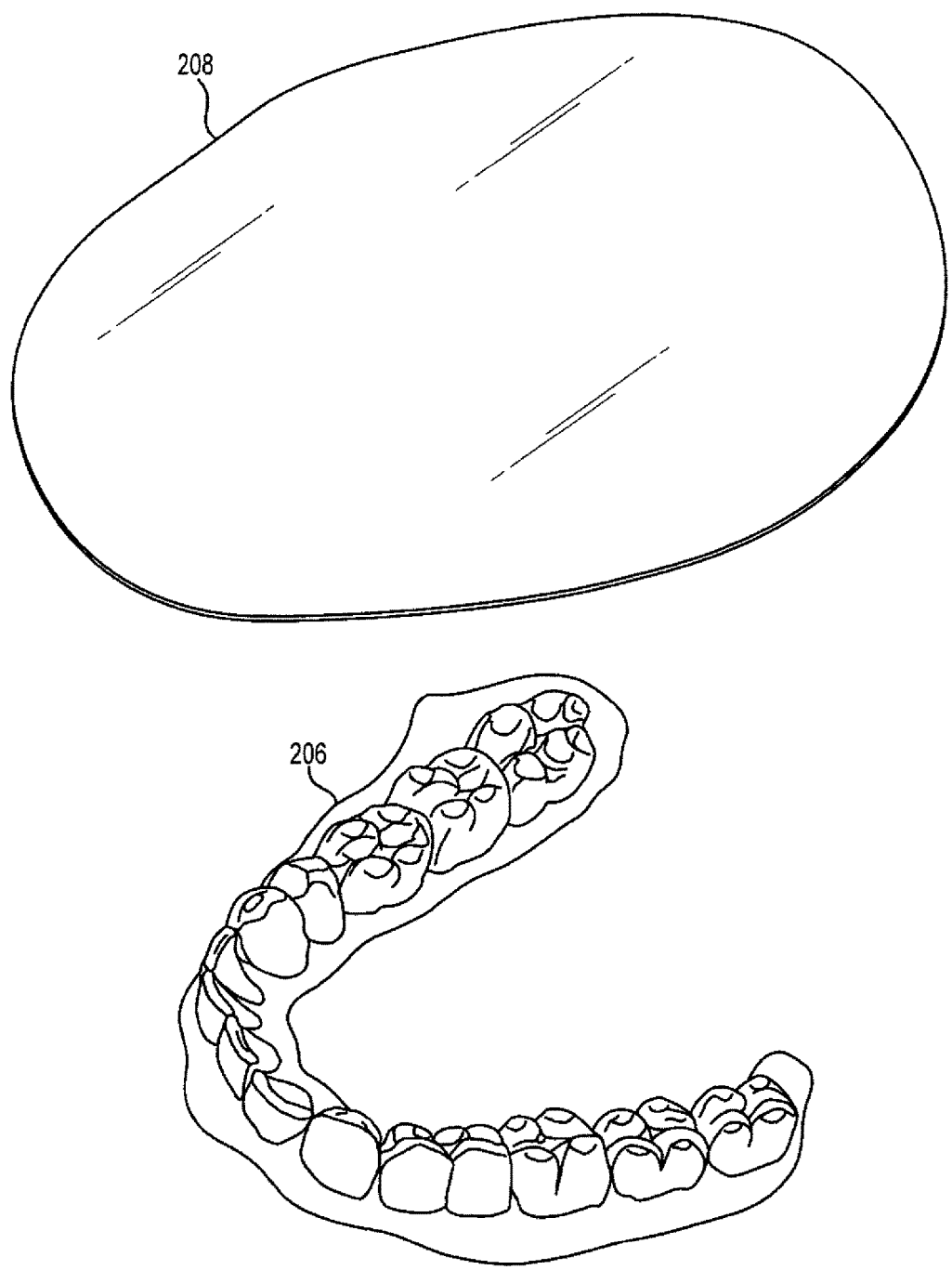
FIG. 2 illustrates a piece of part material being applied over a mold according to one or more embodiments of the present disclosure.

FIG. 2 illustrates a piece of part material being applied over a mold according to one or more embodiments of the present disclosure. With respect to the scope of the present disclosure, the mold can be in any suitable shape. For example, in the embodiment illustrated in FIG. 2, the mold 206 is in the shape of a set of teeth of a jaw of a patient to be treated with a dental aligner appliance.

The part is formed over the mold 206 through use of a sheet of material 208. In this instance, the material is a polyurethane material, but other suitable part materials can be utilized for shaping parts on a mold.

Figure 3:
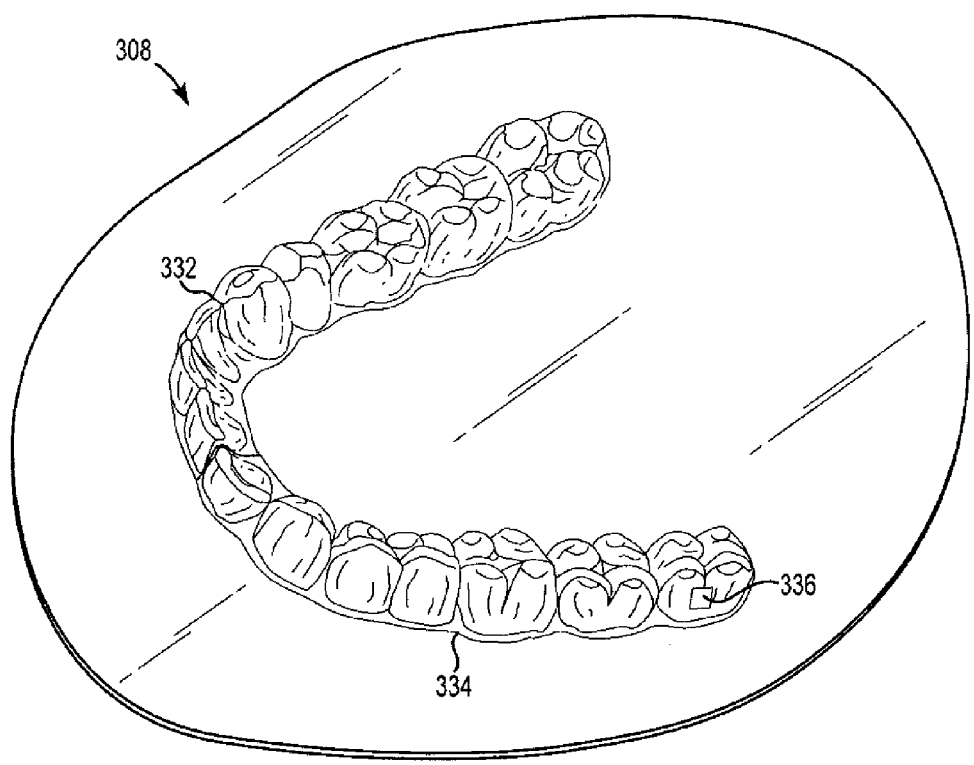
FIG. 3 illustrates a part being created by forming the piece of part material over at least a portion of the surface of the mold according to one or more embodiments of the present disclosure.

FIG. 3 illustrates a part being created by forming the piece of part material over at least a portion of the surface mold according to one or more embodiments of the present disclosure. For example, FIG. 3 illustrates the part created from the sheet of material 208 being formed over the mold 206. This method can be performed by a system, such as, for example, system 100 previously described in connection with FIG. 1.

In the embodiment of FIG. 3, the sheet of material 308 has been formed over the mold to create the part 332 (e.g., a dental appliance). FIG. 3 also illustrates a cut path 334 where a laser beam has cut the part from the sheet of material 308 and a cut path 336 where a feature (e.g., a square shaped window) of the appliance has been cut into the part 332.

In the dental appliance field, parts may be cut through use of a rotary cutting tool and, as such, cutting along the edge of the part could only be done and the resultant cut had rough edges that needed to be polished by hand or by a polishing process before it could be sent to a patient. Embodiments of the present disclosure allow cuts to be made in other positions on the part (e.g., creating a feature such as window 336) and reduce or eliminate the need for post cutting polishing, among other benefits.

Figure 4:
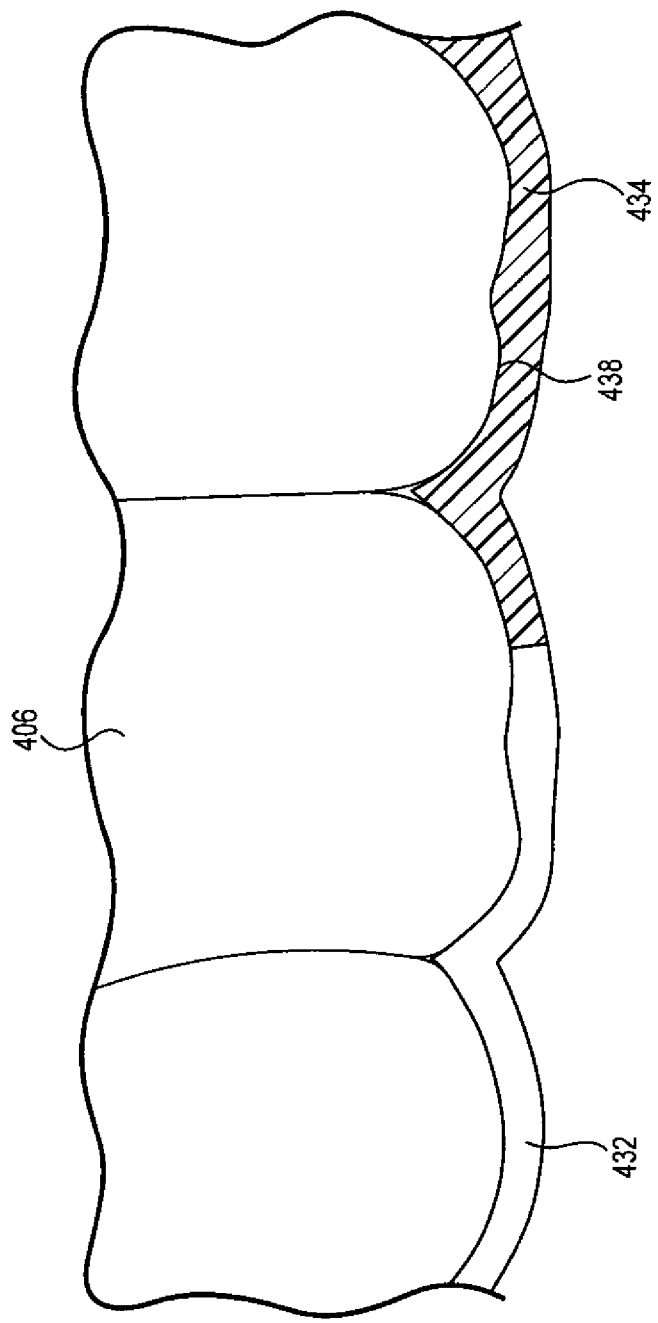
FIG. 4 illustrates a cut path on a part according to one or more embodiments of the present disclosure.

FIG. 4 is a cutaway top view taken at the cut path illustrating a cut path on a part according to one or more embodiments of the present disclosure. In the embodiment illustrated in FIG. 4, the sheet of material 432 used to create the part is positioned over the mold 406 thereby forming top and side portions that will become the dental appliance. In this view, a side portion formed adjacent to the side surface of the mold is shown. As further illustrated in FIG. 2, the mold 206 and 406 is in the shape of a patient's teeth and the resultant part after trimming the excess material is a dental aligner appliance 532 (see FIG. 5). In the embodiment of FIG. 4, a cut path 434 is shown where the laser beam has cut the sheet of material 432 a portion of the way along the cut path. The hash marked area is representative of the sheet of material below the cut path. In this embodiment, the cut path 434 has been cut through the sheet of material 432, but has not cut into the surface 438 of the mold 406.

In some applications, such as when a sheet of material is formed on a mold, it may change the thickness of some portions of the sheet as it conforms to the mold shape. In such instances, in order to provide an appropriate amount of laser beam energy to cut through the sheet of material, but not cut the mold material or cut into the mold material in a substantial manner (e.g., the laser energy can be used to cut through the part material and into an outer surface of the mold material, but does not cut through the mold, thereby maintaining the integrity of the mold), the thickness of the material along the cut path can be measured or estimated (e.g., through virtual modeling of the formation process).

For instance, in some embodiments, a scanning device can be used to dynamically (i.e., just prior to and/or as the cutting is taking place) provide the thickness of the part (e.g., sheet material) before it is cut. In various embodiments, a sensor can be used for measuring and/or sensing the thickness of the part along the cutting path 434. The sensor can, for example, be positioned to measure the thickness of the part along the cutting path at a position immediately prior to the laser beam cutting the part at that position. Sensors can also be utilized to dynamically provide the thickness of the part before it is cut.

If the thickness is estimated, it can be based, for example, on virtual modeling and/or experiential data stored in memory. In some embodiments, the thickness along the cut path can be determined for each point along the cut path, estimated for certain lengths along the cut path (e.g., 1 mm line segments) or estimated for the entire length of the cut path. In some embodiments, the thickness of the part along the cut path has been predetermined prior to commencement of the cutting operation virtually or by measuring the actual thickness of the part using contact or non-contact thickness measuring tools. Accordingly, any suitable measurement tool can be utilized within the scope of various embodiments discussed herein.

Figure 5:
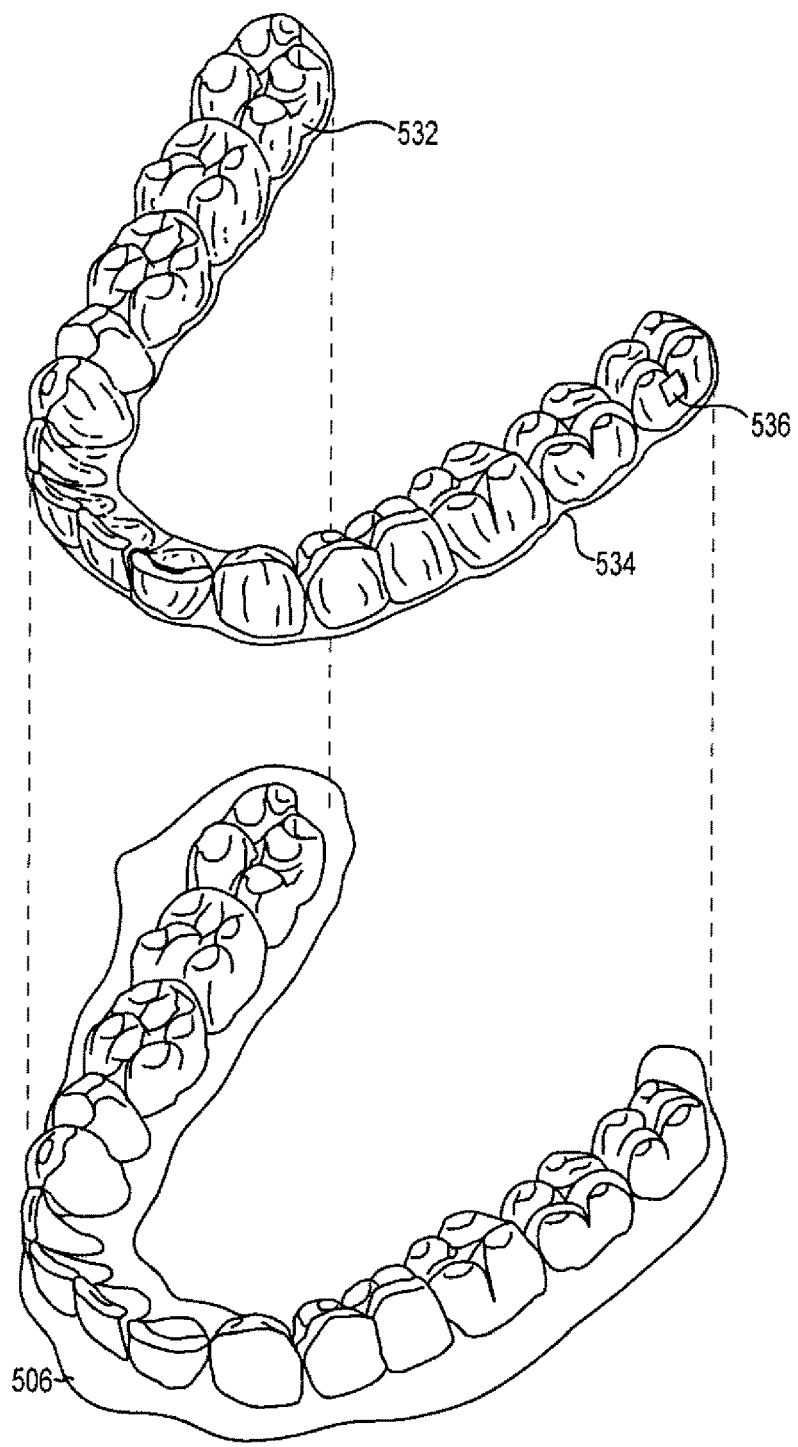
FIG. 5 illustrates the cut part being removed from the mold according to one or more embodiments of the present disclosure.

FIG. 5 illustrates the cut part being removed from the mold according to one or more embodiments of the present disclosure. In the embodiment illustrated in FIG. 5, the part 532 has been cut along the cut path 534, the feature 536 has been cut into the part 532, and the part has been removed from the mold 506. The mold has not been cut by the laser beam and, therefore, it can be reused, if desired.

Figure 6:
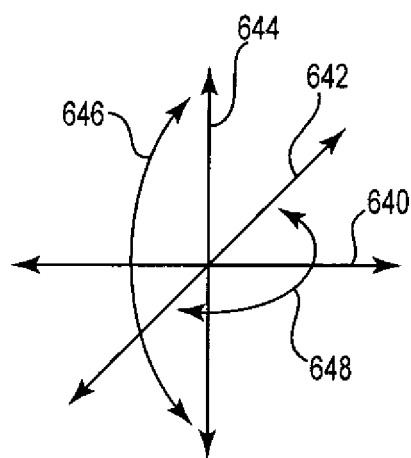
FIG. 6 illustrates one example of five axis movement types that can be used according to one or more embodiments of the present disclosure.

FIG. 6 illustrates one example of five axis movement types that can be used according to one or more embodiments of the present disclosure. In this illustration, the five axes of motion that are provided in the embodiment of FIG. 1 are illustrated.

For example, control mechanism 128 provides motion in the directions 644, control mechanism 124 provides motion in the directions 640 and 646, and control mechanism 126 provides motion in the directions 648. In some embodiments, a control mechanism can be implemented to provide motion in directions 642. This motion could be provided, for example, by control mechanisms 122, 124, and/or 128 or could be provided by another mechanism not shown.

Figure 7:
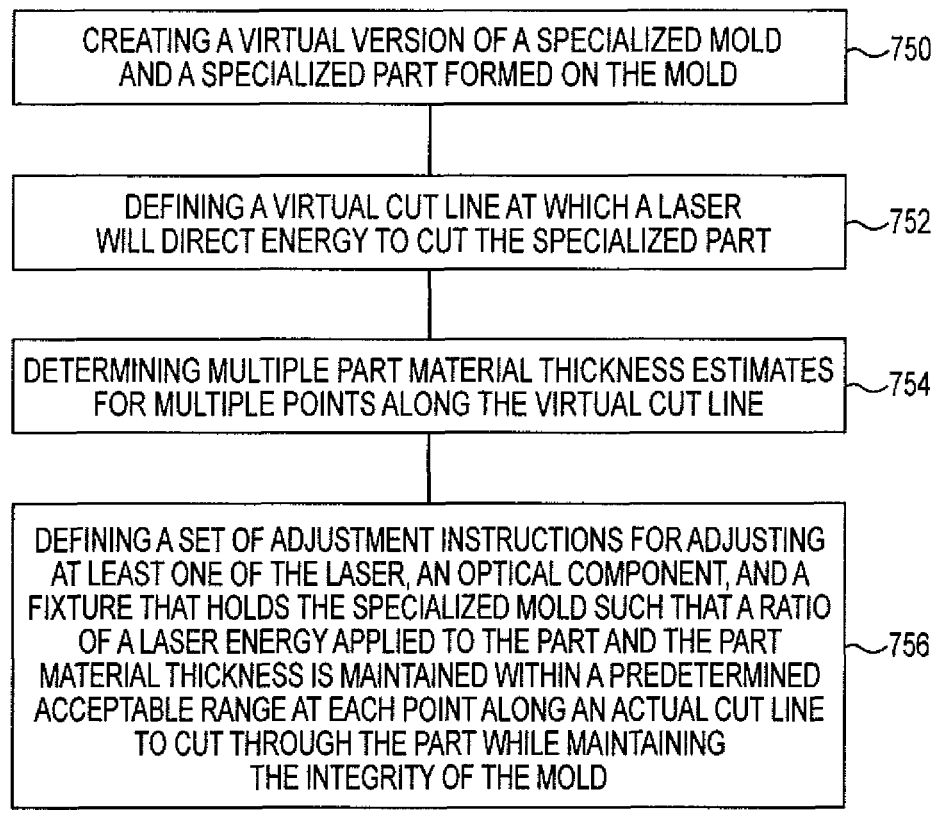
FIG. 7 illustrates a method according to one or more embodiments of the present disclosure.

FIG. 7 illustrates a method according to one or more embodiments of the present disclosure. This method can be performed by a system, such as, for example, system 100 previously described in connection with FIG. 1.

In the embodiment of FIG. 7, the method includes creating a virtual version of a specialized mold and a specialized part positioned on the mold, at block 750. In some embodiments, creating the specialized mold for creating the specialized part to be positioned on the mold includes creating a virtual project development plan or treatment plan wherein the mold is a representation of a form factor of the mold during the virtual development or treatment plan. In some embodiments the method includes creating a virtual mold based on the virtual treatment plan or development plan and wherein the multiple part material thickness estimates for multiple points along the virtual cut path are determined based upon analysis of the virtual mold.

Some method embodiments can include creating a number of specialized molds, each representing a unique part within a respective portion of the virtual project development plan or treatment plan. For example, some methods include creating a number of specialized molds where each specialized mold represents a unique arrangement of teeth along a treatment plan for incrementally moving teeth. In some embodiments having a number of specialized molds, the method includes creating multiple virtual molds based on the virtual treatment plan and wherein the multiple part material thickness estimates for multiple points along the virtual cut path are determined for each virtual mold individually based upon analysis of each virtual mold.

The method also includes defining a virtual cut path at which a laser generating component will direct energy to cut the specialized part, at block 752. In some embodiments, the method includes defining multiple cut paths wherein one of the multiple cut paths represents a portion of the path along a gum line of a patient. Method embodiments can also include defining multiple cut paths wherein one of the multiple cut paths represents a cut on the part that is not along a gum line of a patient.

At block 754, the method includes determining multiple part material thickness estimates for multiple points along the virtual cut path. The method also includes defining a set of adjustment instructions for adjusting at least one of the laser generating components, an optical component, and a fixture that holds the specialized mold such that a ratio of a laser energy applied to the part and the part material thickness is maintained within a predetermined acceptable range at each point along an actual cut path to cut through the part while maintaining the integrity of the support, at block 756.

In various embodiments having a number of specialized molds, defining the set of adjustment instructions can include defining a set of movement and speed adjustment instructions for each virtual mold. In some embodiments, defining the set of adjustment instructions includes defining a set of movement and speed adjustment instructions for moving the fixture with the part positioned on the mold, wherein the instructions adjust the speed of movement of the part past the laser beam based on the determined part material thickness estimates such that the ratio of the laser energy applied to the part and the part material thickness is maintained within the predetermined acceptable range. In some such embodiments, defining the set of movement and speed adjustment instructions can include defining movement and speed of the fixture in five axes in relation to an orientation of the laser generating component.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of supports" can refer to one or more supports.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A method of laser cutting, comprising:
    creating, via a computing device, a virtual version of a mold and a specialized part formed on the mold;
    defining, via a computing device, a virtual cut path at which a laser will direct energy to cut the specialized part formed on the mold;
    determining, via a computing device, multiple part material thickness estimates for multiple points along the virtual cut path;
    defining a set of adjustment instructions for adjusting at least one of the laser, at least one of a mirror or lens, and a fixture that holds the mold with the specialized part formed thereon;
    executing the instructions via a computing device, such that a ratio of a laser energy applied to the specialized part and a part material thickness based on the part material thickness estimates is maintained within a predetermined acceptable range at each point along an actual cut path to cut through the part while maintaining the integrity of the mold;
    blowing gas, via a gas dispensing nozzle, at a point at which the laser contacts the specialized part to blow debris of the specialized part from the cut path; and
    removing the debris via a suction tube located proximate to the point at which the laser contacts the specialized part.

2. The method of claim 1, wherein blowing gas via the gas dispensing nozzle includes blowing chilled gas at the point at which the laser contacts the specialized part to cool the specialized part.

3. The method of claim 1, wherein blowing gas via the gas dispensing nozzle includes blowing heated gas at the point at which the laser contacts the specialized part to heat the specialized part.

4. The method of claim 1, wherein defining the set of adjustment instructions includes:
    defining a set of movement and speed adjustment instructions for moving the fixture with the part positioned on the mold;
    wherein the instructions adjust the speed of movement of the part relative to the laser beam based on the determined part material thickness estimates such that the ratio of the laser energy applied to the part and the part material thickness is maintained within the predetermined acceptable range.

5. The method of claim 4, wherein defining the set of movement and speed adjustment instructions includes defining movement and speed of the fixture in five axes in relation to an orientation of the laser.

6. The method of claim 1, wherein the mold is in the shape of a set of teeth of a jaw of a patient to be treated with the dental aligner appliance.

* * * * *